United States Patent [19]

Smith, III

[11] 4,007,089

[45] Feb. 8, 1977

[54] METHOD FOR BINDING BIOLOGICALLY ACTIVE COMPOUNDS

[75] Inventor: Nathan L. Smith, III, Miami, Fla.

[73] Assignee: Nelson Research & Development Company, Irvine, Calif.

[22] Filed: Apr. 30, 1975

[21] Appl. No.: 573,363

[52] U.S. Cl. .................................. 195/68; 195/63; 195/DIG. 11; 260/112 R; 204/159.12; 204/160.1

[51] Int. Cl.$^2$ ...................... C07G 7/02; C07G 7/00

[58] Field of Search ............... 195/63, 68, DIG. 11; 204/159.12, 159.14, 160.1; 260/112

[56] References Cited

UNITED STATES PATENTS

| | | | |
|---|---|---|---|
| 3,824,150 | 7/1974 | Lilly et al. ........................... | 195/63 |
| 3,843,447 | 10/1974 | Burkoth ............................... | 195/68 |

*Primary Examiner*—Lionel M. Shapiro
*Attorney, Agent, or Firm*—Martin A. Voet

[57] ABSTRACT

A method for binding biologically active compounds to carriers comprising reacting an asymmetric bifunctional linking compound having at least one phenyl azide moiety and at least one s-triazine moiety with a carrier in the presence of light to form a carrier bound to the linking compound through the phenyl azide moiety, and reacting said carrier bound to the linking compound with a biologically active compound under reaction conditions sufficient to bind the biologically active compound to the linking compound through the s-triazine moiety.

7 Claims, No Drawings

METHOD FOR BINDING BIOLOGICALLY ACTIVE COMPOUNDS

BACKGROUND OF THE INVENTION

1. Field of the Invention

The invention relates to a novel method for covalently binding biologically active compounds to carriers and to the complex formed by the method. More particularly, the invention relates to a novel method for covalently binding enzymes to carriers and to the complex formed by the method.

2. Background of the Prior Art

It is known that proteins such as enzymes may be bound onto or into water-insoluble carriers to form bound or "immobilized" enzymes. These immobilized enzymes may be used in various reactions especially in commercial applications, e.g. food processing. Most prior art methods for immobilizing enzymes to carriers require the presence of functional groups in the carrier, usually nucleophilic groups. The present invention does not have such a requirement. U.S. Pat. No. 3,824,150 describes enzymes bound to polymeric sheets with a triazine bridging group.

SUMMARY OF THE INVENTION

The invention relates to a method for binding biologically active compounds to carriers comprising reacting an asymmetric bifunctional linking compound having at least one phenyl azide moiety and at least one s-triazine moiety with a carrier in the presence of light to form a reaction product comprising the carrier covalently bound to the linking compound through the phenyl azide moiety and further reacting said reaction product with a biologically active compound to form a final product comprising the reaction product having the biologically active compound covalently bound to the linking compound through the s-triazine moiety.

The invention further relates to a complex comprising an asymmetric bifunctional linking compound having at least one phenyl azide moiety and at least one s-triazine moiety, said phenyl azide moiety being covalently bound to a carrier.

The invention also relates to a complex comprising an asymmetric bifunctional linking compound having at least one phenyl azide moiety and at least one s-triazine moiety, said phenyl azide moiety being covalently bound to a polymer.

The invention also relates to a complex comprising an asymmetric bifunctional linking compound having at least one phenyl azide moiety linked to a carrier and at least one s-triazine moiety linked to a protein.

DETAILED DESCRIPTION OF THE INVENTION

The asymmetric bifunctional linking compound which may be used in the present invention must have at least one phenyl azide moiety and at least one s-triazine moiety. These linking compounds per se do not form a part of this invention but form the subject matter of co-pending U.S. patent application Ser. No. 573,364 filed Apr. 30, 1975.

Linking compounds which satisfy the foregoing criteria include those compounds having the structural formula

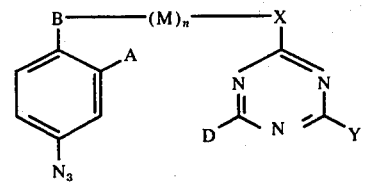

where B is NR, O, S,

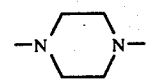

or $CH_2$; $(M)_n$ is a saturated or unsaturated hydrocarbon chain; X is NR, O or S; A is $SO_2R$, CN, $NO_2$ or H; Y is $NR_2$, $N_3$, halogen or SH; R is H and/or a lower alkyl group; D is $N_3$ or halogen and $n$ is 1–12.

A preferred linking compound has the following structural formula

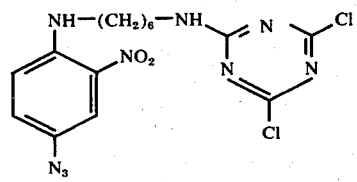

The linking compounds described herein are asymmetric bifunctional compounds. One functional moiety is a phenyl azide. This functionality may be used because of its photochemical reactivity to form a nitrene which inserts into covalent bonds e.g. —C—H, C=C and C—O, of many polymeric organic molecules. The second functional moiety is an s-triazine group which reacts with biologically active compounds such as proteins, as discussed in more detail below.

Carriers which may be used in this invention include polymeric and non-polymeric carriers. Polymers which may be used as carriers are water insoluble organic polymers of synthetic or natural origin. These polymers all react with the phenyl azide moiety of the linking compound. Examples of suitable carriers include polyethylene (conventional and linear), polypropylene, polymethylpentene, ethylene propylene copolymer, polystyrenes, polycarbonate, polyvinyl chloride, etc.; organic polymers from biological origin, such as, for example, cellulose, starch, pectin, etc. and proteins such as enzymes, lipoproteins, mucopolysaccharides, antibodies, etc. Other suitable polymers include aminoethylated cellulose, diazobenzyl cellulose, diazotized p-aminobenzyl cellulose, amino-s-triazine cellulose, acid chlorides of carboxylic or sulfonic acid ion-exchange resins, carboxymethyl cellulose azide bromoacetyl cellulose, methacrylic acid-methacrylic acid-3-fluoro-4,6-dinitroanilide copolymers, the diazotized-m-aminobenzyloxy-methyl ether of cellulose, diazotized poly-p-aminostyrene, the diazotized copolymer of p-aminophenylalanine and leucine, phosgenized poly-p-aminostyrene, ethylene-maleic anhydride copolymers, polyisothiocyanate derivatives of poly-p-aminostyrene, polystyrylmercuric acetate, acrylamide-methylene-bis acrylamide copolymer gels, polyacrylamide, poly-4-hydroxy-3-nitrostyrene and the like.

Examples of carbonyl polymeric carriers which may be used herein include those produced according to any known procedure from such aldehyde monomers as acrolein; α-alkyl acroleins, e.g. methacrolein, α-propylacrylein; crotonaldehyde; 2-methyl-2-butenal; 2,3-dimethyl-2-butenal; 2-ethyl-2-hexenal; 2-decenal; 2-dodecenal; 2-methyl-2-pentenal; 2-tetradecenal and the like, alone or in admixture with up to 95 percent, by weight, based on the total weight of the copolymer, of each other and/or such other copolymerizable monomers known to react therewith such as unsaturated alcohol esters, e.g., the allyl, crotyl, vinyl, butenyl, etc., esters of saturated and unsaturated aliphatic and aromatic monobasic and poly-basic acids such as acetic, propionic, butyric, valeric, adipic, maleic, fumaric, benzoic, phthalic, terephthalic, etc., acids; vinyl cyclic compounds (including monvinyl aromatic hydrocarbons) e.g., styrenes, o-, m-, and p-chlorostyrenes, -bromostyrenes, -fluorostyrenes, -methylstyrenes, -ethylstyrenes, various polysubstituted styrenes, e.g., di-, tri-, and tetrachlorostyrenes, -bromostyrenes, etc.; vinyl naphthalene, vinyl chloride, divinyl benzene, allyl benzene, vinyl pyridine, diallyl benzene, various α-substituted and α-substituted, ring-substituted styrenes, e.g., α-methyl styrene, α-methyl styrene, α-methyl-p-methyl styrene, etc., unsaturated ethers, e.g. ethylvinylether, etc., unsaturated amides, e.g., acrylamide, methacrylamide, etc.; N-substituted acrylamides, e.g., N-methylolacrylamide, N-allyl acrylamide, N-methyl acrylamide, etc.; acrylates such as the methyl, ethyl, propyl, butyl, etc., acrylates and methacrylates; nitriles such as acrylonitrile and other comonomers shown, for example, in U.S. Pat. No. 2,657,192.

Examples of other carbonyl polymers which may be utilized as carriers herein include those produced according to any known procedure and in amounts similar to those indicated above in regard to the aldehyde polymers from such ketone monomers as methyl vinyl ketone, methyl allyl ketone, ethyl vinyl ketone, methyl isopropenyl ketone, ethyl allyl ketone, etc., phenyl vinyl ketone, p-tolyvinyl ketone. Also, such polymers as poly(vinylpyridinium ketones) and haloketones; copolymers of the above-mentioned aldehyde monomers and ketone monomers with or without the above-disclosed copolymerizable comonomers; polyacetal and the like. The molecular weights of the polymers used is not critical and those as low as 1,000 can be used.

Similarly, such polymers as the copolymers of ethylene and carbon monoxide and various glyoxal adducts, all well known in the art, can be utilized herein.

The compounds defined as biologically active compounds include a broad variety of compounds. Suitable biologically active compounds include proteins broadly, that is, compounds which consist of or contain protein. One major class of proteins are compounds which can be broken down from proteins, and enzymes, such as, for example those conventionally used commercially and industrially, e.g. in the fields of tanning of leather, beer-making, sugar processing, etc. Thousands of enzymes are known to exist.

Exemplary of the enzymes which may be utilized herein include proteolytic enzymes, hydrolases, amylases, dehydrogenases, kinases, oxidases, deaminases, amidases, enzyme anticoagulants, etc., including lactic dehydrogenase, creatine, phosphokinase, trypsin, papain, alk. phosphatase, amyloglucosidase, dextranase, glucose oxidase, glucose isomerase, amidase, penicillin amidase, chymotrypsin, β-galactosidase, pyruvate kinase, ficin, pepsin, carboxypeptidase, streptokinase, plasminogen, urease, invertase, alcohol dehydrogenase diastase, β-glycosidase, maltase, aldolase, lactase, amygdalase, lipase, steapsin, erepsin, zymase, catalase, melibiase, pectolase, protease, bovine erythrocyte and/or horse serum chlolinestrerase, tyrosinase, L-asparaginase, glucose isomerase, cytase, adenase, guanidase, carboxylase, inulase, vinegar oxidase aldehydase, rhamnase, myrosinase, phytase, tannase, carbamase, nuclease, guanase, adenase, thrombase, chymase, cozymase and the like.

Other proteins which may be used in the invention include antigens, antibodies, peptides, amino acids, lipoproteins, co-enzymes, etc.

Other biologically active compounds which may be used in this invention include carbohydrates, enzyme inhibitors, biologic markers e.g. radioactively labeled compounds and dyes, and drugs.

Generally, the reaction is carried out in two separate steps. In step one, the phenyl azide moiety of the bifunctional linking compound is linked to a polymeric carrier by photochemical reaction. To carry out the reaction, a bifunctional linking compound, as described above, is reacted with a polymeric carrier in a suitable solvent and exposed to light at a wavelength of about 350 to about 800 nm and preferably about 420 to about 500 nm for about 0.1 to about 60 minutes at temperatures ranging from about −20° to about 50° C and preferably for about 0.5 to about 2 minutes at temperatures between about 0° and 25° C. Upon completion of the reaction, unbound linking agent is removed from the reaction mixture, e.g., by washing with a suitable solvent. In step two, the polymeric carrier with covalently bound linking reagent is incubated with a biologically active compound, e.g., an enzyme, for about 0.5 to about 2 hours at a temperature of about 0° to about 30° C and at a pH of about 4.5 to about 6.5. During this reaction, the s-triazine moiety reacts with the biologically active compound. The phenyl azide-polymer bond is not affected by this reaction. Unbound biologically active compound is then removed from the reaction mixture, e.g., by washing with a suitable solvent. The resultant complex consists of a biologically active compound such as an enzyme bound through the bifunctional linking compound to a polymeric carrier. The complex formed by step 1 is also useful in that the biologically active compound may be added to the complex at a later time.

An alternative method for covalently binding biologically active compounds to a polymeric carriers is to activate the carrier with the s-triazinyl azide derivative of the preferred linking reagent. The activated carrier is then incubated with the biologically active compound at 0° to about 5° C for about 1 to about 20 minutes while illuminating the ultraviolet light of 180 to about 350 nm, preferably 200 to about 300 nm. The excess non-bound biologically active compound is removed as described previously under the general reaction. This alternative method is the preferred method when the biologically active compound contains no nucleophilic groups or when the linking reaction (the nucleophilic replacement reaction) may be detrimental to the biological activity of the biologically active compound. This alternative method would not be the method of choice when the biologically active compound is a protein for the reason that proteins may be damaged by ultraviolet irradiation.

The insolubilized enzymes of the invention can be used in a wide variety of enzymatically catalyzed reactions, and are often suitable for use in processes in which soluble enzymes have previously been used. Thus they may, for example, be used in the preparation of penicillins, beer clarification, the preparation of glucose using amyloglucosidase, the preparation of optically active amino acids, and the formation of L-alanine by transamination. Other potential uses include enzymatic hydrolysis of carbohydrates and proteins, the processing of waste materials, the specific manipulation of large natural molecules such as steroids, alkaloids, chloramphenicol and riboflavine, alcoholic and other kinds of fermentation, the fixing of nitrogen, a luciferase system for A.T.P. estimation, biochemical fuel-cells, and the specific oxidation and reduction of organic materials, including carbon dioxide fixation.

The insolubilized enzymes may also be used in enzymatic analysis, particularly in the sequential analysis of proteins, RNA and DNA. In this case the substrate can be, for example, forced through a permeable sheet by means of a syringe. Where chromatography follows the reaction, it may be possible to chromatograph the substrate across a permeable sheet containing the enzyme, for example in urea analysis.

The following is an example of the foregoing method.

EXAMPLE I

Method of immobilizing glucose-6-phosphate dehydrogenase to polycarbonate

Two mg of the linking compound 1-N-(2-nitro-4-azidophenyl)-6-N-(4,6-dichloro-sym-triazinyl)-diaminohexane having the structural formula

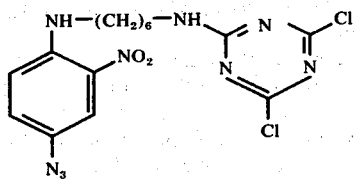

was dissolved in 100 ml ethyl alcohol and 2 ml of this solution was placed in a polycarbonate test tube and exposed to sunlight at ambient temperature for about 20 minutes. The test tube was washed with ethanol to remove unbound linking compound and an enzyme solution, made by adding 10 $\mu$g glucose-6-phosphate dehydrogenase to 2 ml of 0.05M Na acetate buffer having a pH of 5.5, was added to the test tube and incubated for 2 hours at ambient temperature. The enzyme solution was then removed and the test tube was twice rinsed with 0.1M Tris buffer to remove any unbound enzyme. Subsequent enzyme assay of the test tube confirmed the presence of bound enzymes. The enzyme-polycarbonate preparation showed no significant decrease in enzyme activity over a period of 60 days after forming the complex.

EXAMPLE II

Method of immobilizing glucose-6-phosphate dehydrogenase to Tygon tubing 3 ml of the linking compound in ethyl alcohol as in Example I was allowed to flow through Tygon tubing, Formula R3603, 1/8 in. I.D. 3/16 O.D., 2 ft long, for 3 minutes under an ultraviolet lamp. The tubing was rinsed 3 times with 5 ml of ethyl alcohol and 2 times with water. One ml of enzyme solution 20 $\mu$g/ml in pH 5.5 acetate buffer was flowed through the tubing for 1 hour at room temperature. The enzyme-tubing complex was washed as in Example I. Subsequent enzyme assay of the tubing confirmed the presence of bound enzyme. The loss of enzyme activity bound in the tubing was negligible over a period of 30 days.

EXAMPLE III

Method of immobilizing hexokinase to polycarbonate

Example I is repeated, except hexokinase is used in the place of glucose-6-phosphate dehydrogenase. Comparable results are obtained.

EXAMPLE IV

Method of immobilizing glucose-6-phosphate dehydrogenase to polystyrene

The method of Example I is used, except polystyrene discs are used in place of polycarbonate and an artificial light source is used as in Example II. Comparable results are obtained.

EXAMPLE V

Method for immobilizing alcohol dehydrogenase to cellulose

Cellulose particles were suspended in 5 ml of the linking reagent (shown in Example I) (2 mg/100 ml in ethyl alcohol), and irradiated with sunlight at ambient temperature. The activated cellulose was washed with 25 ml of ethyl alcohol. 50 mg of the activated cellulose was incubated with 0.1 ml of alcohol dehydrogenase solution (100 mg/ml pH 5.5 acetate) for 95 minutes at 25° C. The enzyme-cellulose complex was washed 3 times in 5 ml 0.1M Tris pH 8.1. An enzyme assay of the cellulose confirmed the presence of the enzyme.

EXAMPLE VI

Method of simultaneously binding glucose-6-phosphate dehydrogenase and alcohol dehydrogenase to cellulose The activated cellulose was prepared as in Example V. 50 ml of the activated cellulose was incubated with a mixture of glucose-6-phosphate dehydrogenase and alcohol dehydrogenase (each 50 mg/ml in acetate pH 5.5) for 1 hr. The cellulose carrier was washed as in Example V. Subsequent enzyme assays confirmed the presence of both enzymes and that the enzymes were bound in direct proportion to the concentration of each enzyme in the solution surrounding the activated carrier. The enzymes were confirmed to be active both individually and when carrying out simultaneous reactions.

EXAMPLE VII

Method of simultaneously binding hexokinase and glucose-6-phosphate dehydrogenase to polycarbonate tubes The method of Example VI is used, except hexokinase and glucose-6-phosphate dehydrogenase are the enzymes used and polycarbonate tubes (as in Example I) are used in place of cellulose.

EXAMPLE VIII

Method of immobilizing bovine serum albumin to cellulose for use as an immunoabsorbent The method of Example V is used except the protein used is bovine serum albumin. The protein-carrier complex thus formed may be used as an immunoabsorbent to remove anti-bovine serum albumin (antibody) from rabbit serum.

EXAMPLE IX

Method of immobilization of antibody to cellulose for use as immunoabsorbent

Example VIII is repeated, except anti-bovine serum albumin antiserum is bound to cellulose by the method shown in Example V. The bound antibody has affinity for bovine serum albumin.

EXAMPLE X

Method of covalently binding glucose-6-phosphate dehydrogenase to bovine serum albumin In this example, the serum protein bovine serum albumin can be considered to be the carrier polymer. The linking reagent was bound to the albumin by illumination (with Hanovia lamp) of a 2 ml solution of albumin (5 mg/ml) and 0.02 ml linking reagent (1 mg/100 ml ethyl alcohol) at 0° C pH 5 acetate for 2 minutes. The excess linking reagent was removed by passing the albumin solution over a Sephadex G-25 column eluted with pH 5.5 sodium acetate at 0° C. The enzyme was bound to the albumin by incubation of 5 mg of enzyme with the albumin at room temperature pH 5.5 for 2 hours. Subsequent analysis confirmed that the two proteins, i.e., albumin and enzyme, were bound to each other.

EXAMPLE XI

Method of binding glucose-6-phosphate dehydrogenase to regenerated cellulose

The method of Example II is used, except cellulose tubing is used instead of Tygon tubing. Comparable results are obtained.

EXAMPLE XII

Method of binding glucose-6-phosphate dehydrogenase to polyethylene

The method of Example II is used, except polyethylene tubing is used instead of Tygon tubing. Comparable results are obtained.

EXAMPLE XIII

Example I is repeated, except the glucose-6-phosphate dehydrogenase is replaced with each of the following enzymes: lactate dehydrogenase 6-phosphogluconate dehydrogenase, trypsin, peonase and amylase. Comparable results are obtained.

I claim:

1. A method for binding biologically active compounds to carriers comprising reacting an asymmetric bifunctional linking compound having the structural formula

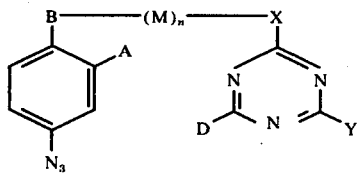

wherein B is selected from the group consisting of NR, O, S,

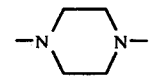

and $CH_2$; $(M)_n$ is a saturated or unsaturated hydrocarbon chain; X is selected from the group consisting of N, R, O and S; A is selected from the group consisting of $SO_2R$, CN, $NO_2$ and H; Y is selected from the group consisting of $N_3$, halogen and SH, R is H or a lower alkyl group, D is $N_3$ or halogen and n is 1-12, with a carrier in the presence of light to form a carrier bound to the linking compound through the phenyl azide moiety, and reacting said carrier bound to the linking compound with a biologically active compound under reaction conditions sufficient to bind the biologically active compound to the linking compound through the s-triazine moiety.

2. The method of claim 1, wherein the biologically active compound is selected from the group consisting of proteins, amino acids, carbohydrates, lipoproteins, coenzymes, enzyme inhibitors and vitamins.

3. The method of claim 1 wherein the biologically active compound is selected from the group consisting of peptides, enzymes, antibodies and antigens.

4. The method of claim 1 wherein the carrier is selected from the group consisting of a synthetic organic polymer and an organic polymer of biological origin.

5. The method of claim 1 wherein the polymer is selected from the group consisting of polyethylene, polypropylene, polymethylpentene, ethylene-propylene copolymer, polystyrene, polycarbonate, and polyvinyl chloride.

6. The method of claim 1 wherein the polymer is selected from the group consisting of cellulose, starch, pectin, mucopolysaccharides, lipoprotein and protein.

7. The method of claim 6 wherein the biologically active compound is selected from the group consisting of peptides, enzymes, antibodies and antigens.

* * * * *